United States Patent
Delwiche et al.

(10) Patent No.: US 6,733,984 B2
(45) Date of Patent: May 11, 2004

(54) SENSOR FOR ANALYZING COMPONENTS OF FLUIDS

(75) Inventors: Michael J. Delwiche, Winters, CA (US); Daniel M. Jenkins, Davis, CA (US); Edward J. Depeters, Davis, CA (US); Robert H. Bondurant, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 399 days.

(21) Appl. No.: 09/839,939

(22) Filed: Apr. 19, 2001

(65) Prior Publication Data

US 2001/0018206 A1 Aug. 30, 2001

Related U.S. Application Data

(62) Division of application No. 09/349,814, filed on Jul. 9, 1999, now Pat. No. 6,287,851.

(51) Int. Cl.⁷ ................................................ C12Q 1/58
(52) U.S. Cl. ....................................................... 435/12
(58) Field of Search .......................................... 435/12

(56) References Cited

U.S. PATENT DOCUMENTS

| | | | |
|---|---|---|---|
| 3,838,034 A | 9/1974 | Groves | |
| 3,907,646 A | 9/1975 | Wilkins | |
| 4,073,694 A | * 2/1978 | Buda et al. .................... | 435/12 |
| 4,131,425 A | 12/1978 | Denney | |
| 4,440,620 A | * 4/1984 | Ono et al. ................ | 204/403.1 |
| 5,008,078 A | 4/1991 | Yaginuma et al. | |
| 5,116,737 A | 5/1992 | McCoy | |
| 5,837,446 A | 11/1998 | Cozzette et al. | |
| 5,858,186 A | 1/1999 | Glass | |
| 5,912,730 A | 6/1999 | Dahm et al. | |

OTHER PUBLICATIONS

Oehler et al., "Detection of gases produced by biological systems with an enzyme–photoacoustic sensor", Infrared Physics 25 (2):319–21 (1985).*
Gonda et al., "Evaluation of dietary nitrogen utilization in dairy cows based on urea concentration in blood, urine and milk", Acta Agriculturae Scandinavica Section A Animal Science 44 (4):236–45 (1994).*
Fuhrmann et al., "Enzymic assays based on the coulometric microflow titration of ammonia and carbon dioxide", Biosensors & Bioelectronics 7(9):319–21 (1992).*
Clana, et al., Robust, reliable biosensor for continuous monitoring of urea during dialysis, Clinical Chemistry, 42(7):1079–1085 (1998).
Das, et al., "Enzyme entrapped inside the reversed micelle in the fabrication of a new urea sensor," Biotechnology and Bioengineering, 54(4):325–332 (1997).
Dazhong, et al., "Sensitive specialization analysis of urea in human blood by surface acoustic wave urea sensor system," Microchemical Journal, 53:6–17 (1996).
Fawcett, et al., "A rapid and precise method for the determination of urea," J. Clin. Path., 13:158–159 (1960).
Hu, et al., "Determination of trace amounts of urea by using flow injection with chemilluminescence detection," Analyst, 119:1829–1833 (1994).
Kazanskaya, et al., "FET–based sensors with robust photosensitive polymer membranes for detection of ammonium ions and urea," Biosensors & Bioelectronics, 11(3):253–261 (1996).
Koncki, et al., "Enzyme biosensor for urea based on a novel pH bulk optode membrane," Biosensors & Bioelectronics, 10:653–659 (1995).
Kriz, et al., "A preliminary study of a biosensor based on flow injection of the recogintion element," Biosensors & Bioelectronics, 11(12):1259–1265 (1996).
Liu, et al., "A new urea sensor based on combining the surface acoustic wave device with urease extracted from green soya bean and its application—determination of urea in human urine," Biosensors & Bioelectronics, 11(4):435–442 (1996).
Marsh, et al., "Determination of urea nitrogen with the diacetyl method and an automatic dialyzing apparatus," J. American Clin. Pathology, 28:681–688 (1957).
Mizutani, et al., "Voltammetric enzyme sensor for urea using mercaptohydroquinons–modified gold electrode as the base transducer," Biosensors & Bioelectronics, 12(4):321–328 (1997).
Poyard, et al., "Performance of urea–sensitive enzyme field effect transistors: Influence of the storage conditions," Biochimia/Biochemistry, 319–257–262 (1996).
Sheppard, et al., "Model of an immobilized enzyme conductimetric urea biosensor," Biosensors & Bioelectronics, 11(10):967–979 (1996).
Skeggs, Leonard T., "An automatic method for colorimetric analysis," J. Amer. Clin. Pathology, 28:311–322 (1957).
Welchselbaum, et al., "A reaction rate method for ammonia and blood urea nitrogen utilizing a pentacyanonitrosyloferrate catalyzed berthelot reaction," Analytical Chemistry, 41(8):848–850 (1969).
Wilcox, et al., "Use of the berthelot reaction in the automated analysis of serum urea nitrogen," Clinical Chemistry, 12(3):151–157 (1996).

\* cited by examiner

Primary Examiner—Sandra E. Saucier
(74) Attorney, Agent, or Firm—Townsend and Townsend and Crew LLP

(57) ABSTRACT

A sensor is provided that is useful for assaying a component of a biological fluid such as blood, urine or milk, and comprises a chamber having an inlet, a liquid containing portion and a vapor containing portion. The liquid and vapor containing portions are in fluid communication. A pressure monitor is in communication with the vapor containing portion and measures pressure change within the vapor containing portion, such as carbon dioxide partial pressure changes which are related to concentration of urea in blood, urine or milk when the enzyme is urease. A method of analyzing a component such as urea in a biological fluid is also provided. Where the biological fluid is dairy milk, milk urea nitrogen to a prediction error of about +/−1 mg/dl may be repeatedly measured in the physiological range of from about 6 to 24 mg/dl.

8 Claims, 2 Drawing Sheets

SENSOR FOR ANALYZING COMPONENTS OF FLUIDS

CROSS-REFERENCES TO RELATED APPLICATIONS

This application is a divisional of and claims the benefit of U.S. application Ser. No. 09/349,814, filed Jul. 9, 1999, now U.S. Pat. No. 6,287,851 disclosure of which is incorporated by reference.

This invention was made with government support under Grant No. 96-34339-3507, awarded by the United States Department of Agriculture. The government has certain rights in this invention.

STATEMENT AS TO RIGHTS TO INVENTIONS MADE UNDER FEDERALLY SPONSORED RESEARCH AND DEVELOPMENT

REFERENCE TO A "SEQUENCE LISTING," A TABLE, OR A COMPUTER PROGRAM LISTING APPENDIX SUBMITTED ON A COMPACT DISK.

FIELD OF THE INVENTION

The present invention generally relates to sensors for the analysis of fluids, and more particularly relates to a sensor that uses liquid samples from fluids such as blood, urine and milk and measures the partial pressure of carbon dioxide as vapor in fluid communication with the liquid sample and generated by an enzymatic reaction, which pressure is related to concentration of a component, such as urea, in the fluid.

BACKGROUND OF THE INVENTION

Because urea is the primary waste carrier of nitrogen for mammals, measurement of dissolved urea is of interest to biomedical, agricultural and environmental professionals. Many techniques for measurement of urea have been developed in the biomedical industry for analyzing biological fluids such as blood or urine so as to monitor renal function and for control of artificial dialysis. For example, U.S. Pat. No. 5,008,078, issued Apr. 16, 1991, inventors Yaginuma et al., describes an analysis element in which gaseous ammonia may be analyzed from liquid samples such as blood, urine, lymph and the like biological fluids. U.S. Pat. No. 5,858,186, issued Jan. 12, 1999, inventor Glass, describes a urea biosensor for hemodialysis monitoring which uses a solid state pH electrode coated with the enzyme urease and is based upon measuring pH change produced by the reaction products of enzyme-catalyzed hydrolysis of urea.

Milk urea is well correlated to urea in the blood and urine, and thus some of the urea measurement techniques used in those fields have been adapted by the dairy industry for measurement of milk urea in order to balance feed rations for optimal nitrogen efficiency. This optimization often leads to considerable savings in feed costs because protein is the most costly feed supplement. In many locations, reduction of nitrogenous waste from the dairy is an even greater consideration than feed costs. Finally, it has been suggested that high systemic urea levels in dairy cows are associated with poor reproductive performance, which is a serious economic concern on dairy farms.

Most existing sensors for urea use the enzyme urease (EC# 3.5.1.5) to hydrolyze urea to ammonium and carbonate. Of these, it is most common to measure changes in the ionic composition of the solution with a pH or other ion selective electrode or by using a conductimetric electrode. These delicate electrodes, however, are susceptible to fouling with the high lipid and protein concentration of milk, thus limiting their use without expensive and complicated filtering or dialysis systems. Furthermore, these sensors are all dependent on the sample pH and buffering capacity.

Two colorimetric assays for urea are commonly used. One involves the reaction of urea with diacetyl monoxime in acid solution to give a pink complex, and another involves the reaction of ammonia from hydrolyzed urea with phenol to produce the blue dye indophenol. For the reaction with diacetyl monoxime, the milk must first be dialyzed to eliminate interferences due to peptides and other amide bonded molecules. Phenol and the catalyst for its reaction with ammonia are highly toxic. For these reasons, these assays are not well suited for farm applications.

Near infrared spectrographic instruments have also been used to provide analysis of materials, such as to determine the urea content of milk. For example, U.S. Pat. No. 5,912,730, issued Jun. 15, 1999, inventors Dahm et al. describes a spectrographic analysis instrument that is said to result in more accurate measurements.

SUMMARY OF THE INVENTION

In one aspect of the present invention, a sensor that is useful for assaying a component of a fluid is provided. The sensor comprises a chamber having an inlet adapted to admit a liquid sample, and further has a liquid containing portion and a vapor containing portion, with the two portions in fluid communication. A pressure monitor is in communication with the vapor containing portion, and is of a construction sufficient to measure pressure changes within the vapor containing portion. The measured pressure changes may be related to concentration of the component of the fluid being assayed.

In one preferred embodiment of the invention, the sample is taken from a biological fluid and is admitted into the liquid containing portion of the chamber. This sample is exposed to an enzyme for which the component of interest is a substrate. The enzyme exposure may be before the sample enters the chamber or during residence of the liquid sample within the chamber. A preferred enzyme is urease, which may be used to assay urea in biological fluids such as milk, urine and blood.

A particularly preferred embodiment of the sensor is where the pressure monitor is calibrated to provide urea (or milk urea nitrogen) concentration and may have a prediction error for milk urea nitrogen of not greater than about +/−1 mg/dl (over a physiological range of from about 6 ml/dl to about 24 ml/dl).

Another aspect of the present invention is a method of analyzing a component in a biological fluid. The analysis method includes the steps of providing a liquid sample of the biological fluid, contacting the sample with an enzyme for which the component is a substrate so as to form carbon dioxide as a reaction product, and detecting the amount of carbon dioxide so formed. One preferred embodiment of the present inventive method is in analyzing milk urea nitrogen (MUN) in dairy milk. In practicing this embodiment, the method comprises providing a dairy milk sample and contacting the sample with urease to yield carbonate and ammonium ions. The equilibrium is shifted towards carbon dioxide by adjusting pH, and carbon dioxide vapor is detected. This detected carbon dioxide may then be related to the concentration of MUN in the dairy milk sample.

Feed costs constitute the largest single expense of the dairy industry. Because of this and the increasing premium placed on milk protein content, there is considerable interest in optimizing nutritional input for the highest milk protein to feed cost ratio. In many localities, there is also concern about the environmental effects of excess nitrogen in dairy waste. Excessive levels of nitrogen in feed are believed to cause high systemic urea nitrogen levels without corresponding increase in milk protein. Use of the sensor and method in accordance with this invention can improve the nitrogen balance in dairy herds for economic benefit to the farmer and environmental benefit to the public.

Sensors of the invention may be used to automatically measure MUN during milking, and can thus be automated to run during an already automated milking process. The inventive sensors can complete one measurement cycle faster than the turn-around time for cows in the parlor (10 min), and are able to repeatably measure MUN to within 1 mg/dl in the physiological range from about 6 to 24 mg/dl.

Other aspects and advantages of this invention may be understood by reading the specification and claims.

DETAILED DESCRIPTION OF THE PREFERRED EMBODIMENTS

Figure 1:
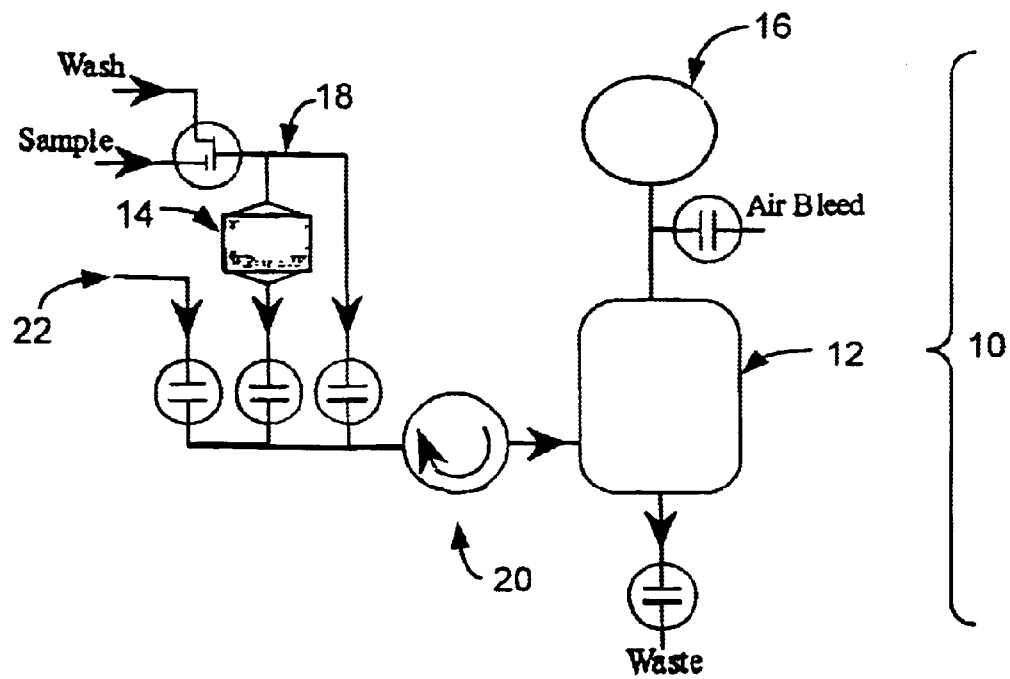
FIG. 1 is a schematic of one sensor embodiment of the invention where enzyme is immobilized.

Sensors of this invention are particularly useful to automatically measure milk urea nitrogen (MUN) during milking, since one measurement cycle can be performed in less than 10 minutes and can repeatedly measure MUN to within 1 mg/dl in the physiological range from about 6 to 24 mg/dl (2.1 to 8.6 mM). The sensor and assay method of the preferred embodiments measure the change in pressure of an enclosed volume in contact with the liquid sample solution when carbonate (a product of urea hydrolysis) is driven in its equilibrium with $CO_2$. The $CO_2$ then is volatilized.

However, use of the inventive sensor and method for other applications are contemplated. Among other applications contemplated are those for diagnostic applications (such as diabetes and other disorders), since metabolic carbohydrates in the citric acid cycle (using various dehydrogenases) generate carbon dioxide, which can be measured by a sensor described herein. Another application contemplated is to assess uric acid (using the enzyme uricase for animal analyses or urate oxidase for human biological fluid analyses). In the catabolism of uric acid to allantoin, which is rate enhanced by urate oxidase, carbon dioxide is again a reaction product (or byproduct). Uric acid is a contaminate in agricultural runoff, such as from the poultry industry. Uric acid analysis is also useful in assessing risk of kidney stones and gout in humans. With some variations made, practice of the invention can also be to determine the presence of an enzyme in a test sample such as soil. For example, ureas in soils lead to accelerated hydrolysis and oxidation of urea (as fertilizer) to ammonia and nitrates which leach into ground water.

Urea is a major component in urine and blood and is present in mammalian milk. Under acidic conditions, the hydrolysis of urea, such as by urease, generates carbonate which exists primarily as dissolved carbon dioxide. A sealed gaseous cavity in contact with the solution will pressurize to an extent proportional to the amount of urea originally in the sample as dissolved $CO_2$ is released into the gaseous phase. Preferred embodiments have a gaseous cavity that has a porous membrane in contact with a test solution which is useful to allow the sensor to operate on a solution stream rather than in a batch mode. A variety of suitable porous membranes are known to the art where the membrane acts as a barrier to liquid permeation but permits passage of gas or vapor therethrough.

The ratio of dissolved carbon dioxide to carbonate is dependent on pH. If the solution is alkaline, the carbonate in the system is effectively ionized in solution. Therefore, the system should be acidified in order to generate a pressure signal in real time. For example, lowering the pH to 4.1 drives 99% of the carbonate to $CO_2$. Shifting the equilibrium between carbonate and carbon dioxide may be accomplished with substantially any acidic pH adjusting agent, such as inorganic or organic acids. As is well known, the partial pressure of a dissolved gas is given by Henry's law. Assuming milk is about 90% water, at 20° C. the equilibrium partial pressure of carbon dioxide in contact with milk would be 1.01 kPa per mg/dl (0.3 mM) of hydrolyzed MUN.

However, the system should not be acidified until the enzymatic reaction has taken place, since the acid will stop the enzymatic reaction. During collection of carbon dioxide from the liquid sample, it is preferable to agitate the chamber to increase the rate of volatilization of dissolved gas in the liquid sample.

Another parameter that has an effect on the system is temperature, since the solubility constant is temperature dependent. Temperature variation effects may be corrected or controlled by the ratio of gaseous and fluid volumes in the chamber design as a means of temperature compensation, or alternatively, temperature compensation may be done in software. Temperature also has an influence on water vapor pressure. This may be compensated for by taking a difference reading between an enzymatically hydrolyzed sample and an untreated sample, which is also appropriate to correct for the effects of background dissolved gases and ambient $CO_2$ and humidity levels.

With reference to FIG. 1, a prototype sensor embodiment 10 is illustrated having a reaction cell or chamber 12, an immobilized enzyme 14 (sometime hereinafter "IMER"), and a pressure transducer or monitor 16. A liquid sample is introduced along pathway 18 which includes a flow path so as to contact the immobilized enzyme 14 and then be pumped by pump 20 into cell 12. Acid is added as shown by 22 (which serves as a pH adjusting agent to drive the equilibrium towards carbon dioxide). Valves 24 are disposed along the pathway 18 to facilitate introduction of acid and to control flow. The reaction cell 12 is not entirely filled with the liquid sample and thus the upper portion is a gas phase into which $CO_2$ passes. Cell 12 is preferably agitated by a shaker or the like (not illustrated) to increase the rate of volatilization of dissolved gas. The pressure monitor 16 is in communication with reaction cell 12 and measures the pressure change from the increasing carbon dioxide partial pressure.

Suitable pressure monitors for use with the invention preferably have a full scale range of about 0–100 kPa with a resolution of about 0.1 kPa, and a use time of less than about 0.1 second.

Figure 2:
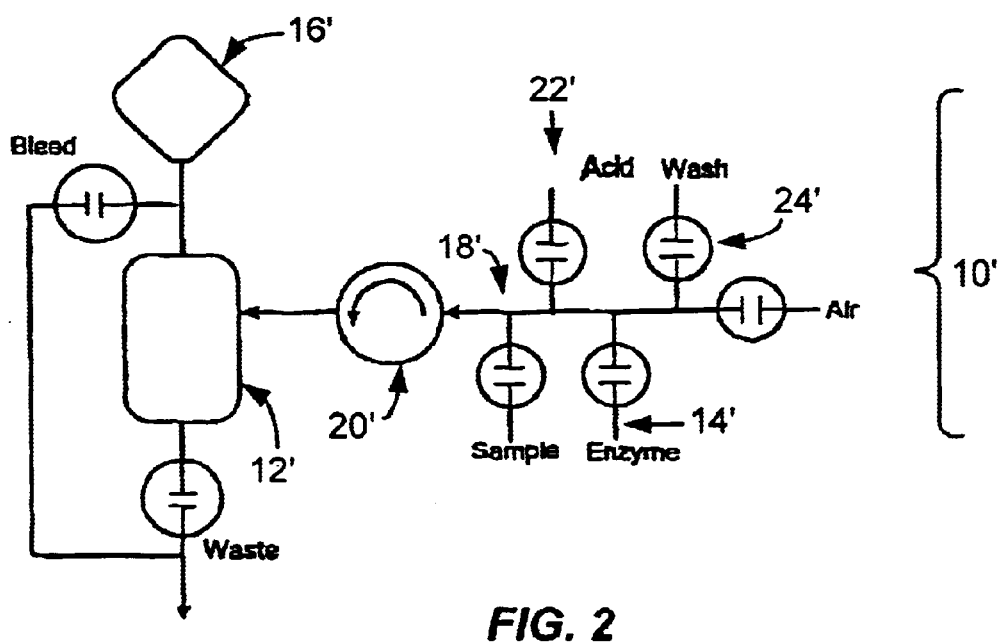
FIG. 2 is a schematic of another sensor embodiment of this invention where enzyme is introduced as a fluid; and, FIG. 3 graphically illustrates practice of the invention where pressure is plotted as a function of time with the solid circles representing practice of the inventive method (and open circles are a control).

Turning to FIG. 2, another prototype sensor embodiment 10' is illustrated having a reaction cell or chamber 12' and a pressure transducer or monitor 16'. A liquid sample is introduced along pathway 18' which includes a flow path to the chamber 12' and can be pumped by pump 20' into chamber 12'. A source of enzyme, such as an aliquot of dissolved enzyme 14' may be added into pathway 18' when desired and then followed by the addition of acid 22'. Again, the pressure monitor 16' is in communication with chamber 12' and measures the pressure change from the increasing carbon dioxide partial pressure. The use of fluid enzyme is preferred. Valves 24' facilitate controlled introduction of the enzyme 14' in fluid form, the introduction of acid 22', and other desired operations (e.g. introduction of air, wash, and disposal of waste).

Figure 3:
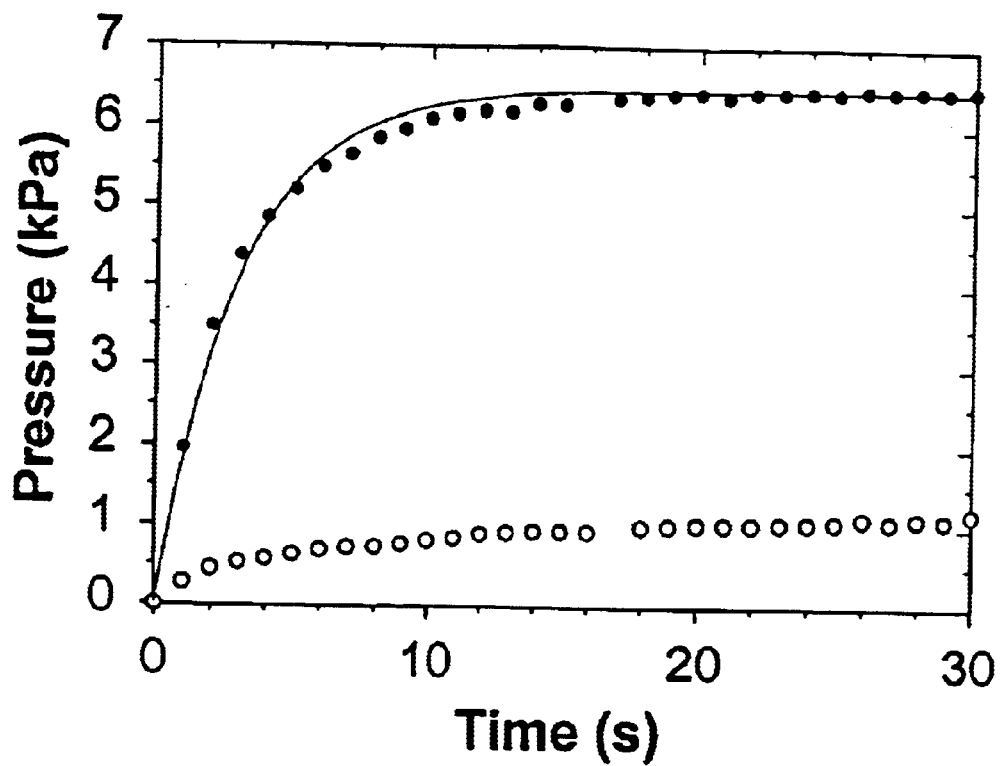

FIG. 3 graphically illustrates pressure recorded versus time during practice of an automated embodiment of the assay, where the solid circles represent enzymatically hydrolyzed sample and the open circles represent untreated sample. FIG. 3 shows the pressure developed by a sensor embodiment over time for a 30 mg/dl urea nitrogen standard. The sensor can be approximated as a first order system with a time constant of ten seconds and, therefore, effectively reaches equilibrium within one minute. This is fast enough to use in an on-line sensor. FIG. 3 also shows that the pressure developed above the untreated sample cannot be neglected if samples are expected to have variable background dissolved gas and the ambient conditions are not controlled.

As will be readily understood and earlier noted, the inventive method can also be practiced so as to analyze for the enzyme itself rather than for the enzyme's substrate. That is, broadly the inventive method can be used to analyze a component (either component) of an enzymatically catalyzed process from a test sample. By enzymatically catalyzed process is meant that the component being analyzed is either the substrate for which the component is the enzyme or is the enzyme for which the component is the substrate. (The enzymatically catalyzed process itself, of course, can involve other moieties, such as cofactors, which will either be present in the test sample or may be supplied during practice of the method.) The test sample itself will typically be a biological fluid, but may also be in other forms when originally obtained. For example, practice of the invention for analyzing an enzyme such as urea in soil is contemplated; however, the test sample (of soil) will then be dissolved or suspended in liquid so as to facilitate the enzymatically catalyzed process.

Aspects of the invention will now be illustrated by the following examples, which serve to illustrate but not limit the invention.

EXAMPLE 1

A manual assay was carried out in a 3.5 ml volume section of plastic tubing attached to the positive port of a 50 kPa pressure transducer (Motorola MPX 2050D, Phoenix, Ariz.). Standards were prepared by dissolving urea or $Na_2CO_3$ in 0.1 M phosphate buffered saline (PBS). We hydrolyzed the urea by adding 1 mg of lyophilized urease (Type IX urease, Sigma Aldrich Chemical Corporation, St. Louis, Mo.) to each 4 ml of standard and incubating at room temperature for 20 minutes. A volume of 2.0 ml of the standard solution was then added into the tubing, followed by 0.4 ml of 1.0 M citric acid to bring the pH below 4.0. The tubing was sealed and shaken by means of a small DC motor with an off-center shaft. When the system reached equilibrium, the signal from the transducer was recorded.

EXAMPLE 2

A prototype sensor (FIG. 1) was made using a miniature positive displacement pump (Bio-Chem Valve Inc., 120SP1250-4, Boonton, N.J.) and six miniature valves (waste valve—General Valve Corp., 3-121-900, Fairfield, N.J.; 3-way valve—The Lee Co., LFAA 1203610H, Westbrook, Conn.; all others—The Lee Co., LFAA 1201710H). The reaction cell was shaken by the same means as the tubing in the manual assay. The operation of these components was computer controlled with a digital interfacing board through high current/voltage Darlington drivers (Motorola ULN 2003A). We used a 10 kPa pressure transducer (Motorola MPX 2010D) to measure the signal. The reaction cell was machined from plastic (Delrin) and held about 1 ml of fluid.

The volume of gas in the cavity of the pressure transducer and in the line between the transducer and the reaction cell was estimated to be 190 $\mu$l. We also estimated the fluid volume in the lines between the reaction cell and the pump and waste valve to be 100 $\mu$l. The stroke volume of the pump was measured to be 52 $\mu$l. The fluid control sequence for the sensor is described in Table 1, with a sample measurement cycle taking less than 8 minutes.

TABLE 1

Fluid Control Seuuence for Sensor

| | |
|---|---|
| (1) | pump 120 strokes of sample through IMER, 1.5 stroke/sec. |
| (2) | pump 12 strokes of sample around IMER with waste valve open, 2 strokes/sec |
| (3) | close waste valve, open air bleed, pump 12 strokes of sample, 2 strokes/sec. |
| (4) | pump 5 strokes of citric acid, 2 strokes/sec. |
| (5) | close all valves, shake reaction cell for 90 seconds, then measure the signal from the transducer (background signal). |
| (6) | open waste valve, pump 20 strokes of wash solution at 4 strokes/sec, wait three seconds, repeat. |
| (7) | open air bleed, close waste valve, pump 20 strokes of wash solution at 4 strokes/see, open air bleed, wait 5 seconds, repeat (6). |
| (8) | open waste valve, close air bleed, pump 12 strokes of sample through IMER, 1.5 strokes/sec. |
| (9) | close waste valve, open air bleed, pump 12 strokes of sample through IMER, 1.5 strokes/sec. |
| (10) | repeat (4) and (5) (measure gross signal). |
| (11) | take difference between gross and background signals. |
| (12) | repeat (6) and (7). |

To hydrolyze the sample in the sensor, urease was entrapped in acrylamide beads which were packed into an immobilized enzyme reactor (IMER). The IMER was a plastic (Delrin) column of 2.38 cm diameter and 0.8 cm depth. The acrylamide beads were prepared by dissolving 20 mg of urease per ml of acrylamide solution. The acrylamide solution used was 7.2% w/v polymer, 5:1 ratio of acrylamide to bisacrylamide dissolved in PBS of pH 7.0. Polymerization was initiated by addition of 1:70 volume ratio of 100 mg/ml sodium persulfate and 1:140 ratio of tetraethylenediamine (TEMED). The polymer was then extruded through a 27 gage hypodermic needle (0.10 mm ID) and rinsed with PBS in a 100 $\mu$m cell strainer. Citric acid (1 M) was used to acidify sample, and the wash solution was PBS with 0.05% Tween 20 (Fisher Scientific, Pittsburgh, Pa.).

The pressure transducer was powered with 12 V and the differential signal was amplified by an adjustable gain instrumentation amplifier. This signal was then filtered with a $6^{th}$ order switched-capacitor low-pass Butterworth filter with cutoff frequency of 21 Hz and an external offset null. The output of this filter was then filtered with a $2^{nd}$ order resistor-capacitor low-pass Butterworth filter with a cutoff frequency of 50 Hz to eliminate the clock noise. The output was measured on a data acquisition board with a sampling rate of 240 Hz. In software the signal was digitally filtered with a 241 coefficient nonrecursive low-pass filter with a cutoff frequency of 20 Hz.

The pressure developed by the sensor over time for a 30 mg/dl urea nitrogen standard was monitored. The sensor can be approximated as a first order system with a time constant of 10 seconds and, therefore, effectively reaches equilibrium within 1 minute. This is fast enough to use in an on-line sensor.

Standard curves for the manual assay on urea and $Na_2CO_3$ standards in buffers of varying pH were prepared, which showed that sensitivity is diminished at lower pH as more $CO_2$ is lost during the incubation period. They also showed that when the pH is high enough to stabilize the carbonate ion, no difference in sensitivity can be observed between carbonate standards and stoichiometrically equivalent hydrolyzed urea standards.

EXAMPLE 3

With reference to FIG. 2, another prototype sensor embodiment 10' was made where the miniature positive displacement pump and the pressure transducer were as described in Example 2. The valves were two-way pinch valves, with the valves used for reagent selection (e.g. enzyme and acid) obtained from Neptune Research as 161P011 and those for waste and bleed as 225P011–21.

In conclusion, a new chemical assay is provided which, for urea, involves enzymatic hydrolysis to ammonium and carbonate and the subsequent measurement of carbon dioxide partial pressure. The assay is simple to implement in an automated version and the hardware involved is not prone to fouling and damage when a biological fluid such as raw milk is being assayed. The assay has no dependence on milk fat in the sample, and the effects of milk proteins and lactose are slight. The assay is especially contemplated for use in an on-line sensor to measure milk urea nitrogen in the milking parlor. The new assay for milk urea is simple and robust. At 24° C., the sensitivity of the assay is 0.367 kPa per mg/dl of urea nitrogen.

It is to be understood that while the invention has been described above in conjunction with preferred specific embodiments, the description and examples are intended to illustrate and not limit the scope of the invention, which is defined by the scope of the appended claims.

What is claimed is:

1. A method of analyzing a component of an enzymatically catalyzed process from a test sample, comprising:
    providing a liquid sample of the test sample;
    contacting the sample either with an enzyme for which the component is a substrate or with a substrate for which the component is an enzyme, wherein the contacting forms carbonate ion in equilibrium with carbon dioxide;
    shifting the equilibrium towards carbon dioxide; and,
    detecting the carbon dioxide as a partial pressure.

2. The method as in a claim 1 wherein the enzymatically catalyzed process is catalyzed by an enzyme selected from the group consisting of urate oxidase, uricase, urease, and a dehydrogenase enzyme.

3. A method of analyzing milk urea nitrogen (MUN) in dairy milk, comprising:
    providing a dairy milk sample;
    contacting the sample with urease, at least one of the dairy milk sample and the urease being in a liquid solution, wherein the contacting forms an equilibrium between carbonate ion and carbon dioxide;
    shifting the equilibrium towards carbon dioxide; and,
    detecting the carbon dioxide as a partial pressure.

4. The method as in claim 3, wherein the equilibrium is shifted by admixing the liquid solution with a pH adjusting agent.

5. The method as in claim 3 further comprising correlating the carbon dioxide detected to the concentration of MUN in the dairy milk sample.

6. The method as in claim 3 wherein the contacting includes agitating the dairy milk sample.

7. The method as in claim 5 wherein the MUN in the dairy milk sample is measured within about +/−1 mg/dl.

8. The method as in claim 3 wherein the urease is immobilized.

* * * * *